US005098415A

United States Patent [19]

Levin

[11] Patent Number: 5,098,415

[45] Date of Patent: Mar. 24, 1992

[54] DEVICE AND METHOD FOR USING AN AQUEOUS SOLUTION CONTAINING OZONE TO TREAT FOOT DISEASES

[76] Inventor: Jack Levin, Place One #529, 777 W. Germantown Pk., Plymouth Meeting, Pa. 19462

[21] Appl. No.: 594,764

[22] Filed: Oct. 9, 1990

[51] Int. Cl.$^5$ .......... A61M 35/00

[52] U.S. Cl. .......... 604/293

[58] Field of Search .......... 604/290, 293; 128/24 R, 128/202.25, 65, 66

[56] References Cited

U.S. PATENT DOCUMENTS

| | | | |
|---|---|---|---|
| 983,907 | 2/1991 | Knips et al. | 128/202.25 |
| 4,331,137 | 5/1982 | Sarui | 604/293 |
| 4,375,812 | 3/1985 | Vaseen et al. | 604/290 |

*Primary Examiner*—Ronald Frinks
*Assistant Examiner*—R. Clarke

[57] ABSTRACT

A device and method for the treatment of foot afflictions using an aqueous solution of ozone comprising container means into which a person inserts at least one foot to be treated and for holding a liquid such as water to be circulated in the device, pump means for circulating a solution of liquid and ozone in the device, production means to permit the transfer of ozone to the container means, controller means for regulating the production of ozone from the ozone production means, dispersion means for dispersing the ozone in the liquid, and leakage protection means to decrease the amount of ozone-containing gas from escaping from the device. The method of treating a person's foot afflictions comprises the steps of placing the person's feet into a container, filling the container with a liquid to cover the afflicted portion of the person's feet, generating ozone gas and mixing/dissolving the ozone gas with the liquid, circulating the mixture/solution about the person's feet for a predetermined time, and removing the person's feet from the container holding the liquid and ozone.

11 Claims, 2 Drawing Sheets

DEVICE AND METHOD FOR USING AN AQUEOUS SOLUTION CONTAINING OZONE TO TREAT FOOT DISEASES

BACKGROUND OF THE INVENTION

The therapeutic benefits of using a bathing solution containing any number of elements compounds and/or chemicals, to cleanse or treat the body or a portion thereof are widely known. Indeed, the art is replete with numerous disclosures of the use of a wide variety of solutions and apparatus for using such solutions in the treatment of physical ailments.

One example of such a device used to bathe a body portion is found in U.S. Pat. No. 4,493,119 issued to Baumann. The Baumann device is used for the treatment of eyes by bathing or washing them in a liquid circulated in an air whirlpool type device which generates oxygen-rich air bubbles.

In addition, numerous examples of treatments utilizing ozone gas ($O_3$) or a solution thereof have been previously disclosed. These treatments rely on the oxidative characteristic of ozone which acts as a bactericide/fungicide/germicide to destroy a wide variety of undesirable and deleterious organisms and growths. For example, U.S. Pat. No. 2,745,407 issued to C.F. Mueller et al., discloses a therapeutic ozone device used to treat the human body with ozone at its orifices. The device comprises a plurality of gas filled glass tubes through which electrical current flows. The tubes are disposed in close parallel proximity to each other so that arc discharges occur between the tubes along substantially their entire length. The arc discharge action in the presence of oxygen, generates ozone for the treatment of such maladies as nasal, ear and other orifice infections.

U.S. Pat. No. 4,422,450 issued to Rusteberg discloses a germicidal periodontal irrigation system which employs a stream of irrigating liquid in which bubbles of ultraviolet-produced ozone are finely dispersed. The flow of the irrigating liquid through an irrigation conduit carries the ozone bubbles to the inflamed areas to effect a germicidal action. Ozonation of the carrier liquid is produced by passing a gas containing oxygen in the immediate vicinity of an irradiating ultraviolet lamp to produce "actinic" ozone, the gas then being bubbled through a storage reservoir from which the irrigating liquid is continuously drained and dispensed, carrying the ozone bubbles along with it.

These devices, while suitable for their intended purposes are very limited in scope due to the fact that the treatment area is small and well-defined, precluding the use of the device to affect larger body parts and/or surfaces.

One device which discloses the use of ozone as a bactericide to maintain the sterility of a liquid solution is used to treat larger body surface areas. This device is disclosed in U.S. Pat. No. 4,375,812 issued to Vasseen et al., for the treatment of a burn patient by immersion in an inert, isotonic liquid which has ozone absorbed therein.

Other diseases and ailments may be controlled or eradicated by having the individual expose the affected area to a liquid solution/mixture containing ozone. For example, many individuals with foot problems would greatly benefit by the use of an aqueous ozone bath. These individuals include, but are not limited to diabetic patients who have diabetic lesions on their feet, persons with fungal infections of the skin, toenails, and/or toenail roots, such as athlete's foot (tinea pedis), trichophyton rubrum, T. mentagrophytes, Epidermphyton floccosum, etc. or other complications such as simple lacerations.

Accordingly, a need exists for a device and method for using an aqueous solution containing ozone to treat foot diseases/afflictions/injuries, which would be alleviated by the oxidative properties of ozone.

OBJECTS OF THE INVENTION

Accordingly, it is a general object of this invention to provide a device and method for using an aqueous solution containing ozone to treat foot diseases which overcomes the disadvantages of the prior art.

It is a further object of this invention to provide a device and method for using an aqueous solution containing ozone in the treatment of fungal foot infections which is effective, safe, and easy to use.

It is yet a further object of this invention to provide a device and method for using an aqueous solution containing ozone for the effective treatment of foot lesions and/or lacerations.

SUMMARY OF THE INVENTION

These and other objects of this invention are achieved by providing a device and method for using an aqueous solution containing ozone in the treatment of foot diseases. The device comprises a container into which a person inserts their foot/feet for treatment. The container also acts as a foot bath to hold the ozonated liquid to be circulated in the device. The device also comprises a pump to circulate the ozonated liquid held in the container, an ozone generator for producing ozone, a controller to regulate the production of ozone from the ozone generator, dispersion apparatus for dispersing the ozonated liquid prior to its injection by the pump into the container, and a leakage protection component to decrease the amount of ozone-containing gas from escaping from the device.

The method of treating foot/feet afflictions with an aqueous solution of ozone comprises the steps of placing the person's foot/feet into a container, filling the container with a liquid to cover the afflicted portion of the person's foot/feet, generating ozone gas and mixing the ozone gas with the liquid, circulating the liquid and ozone about the person's foot/feet for a predetermined time, and removing the person's foot/feet from the container holding the liquid and ozone.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENT

Figure 1:
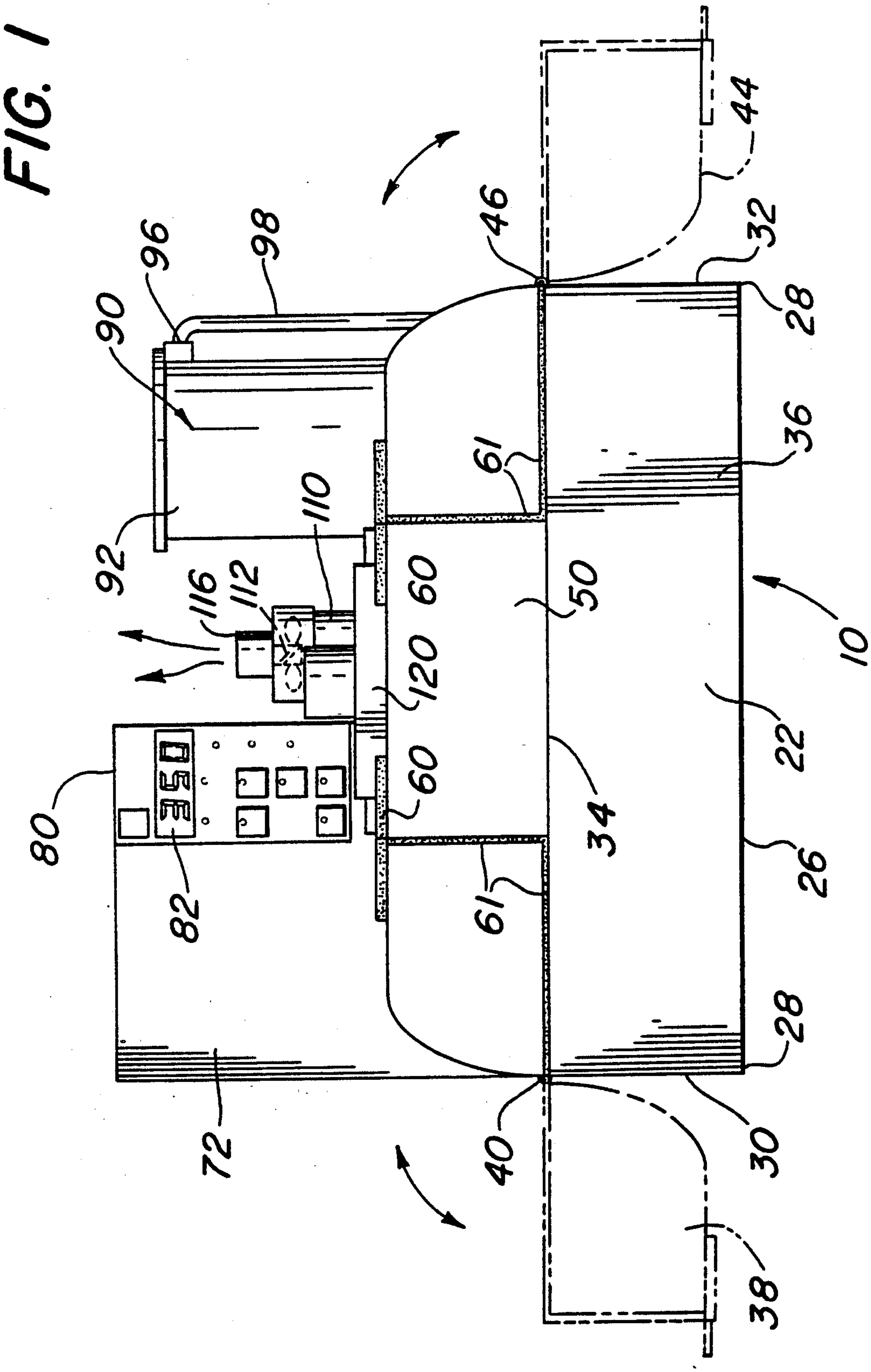
FIG. 1 is a side view of a device constructed in accordance with the present invention.
Figure 3:
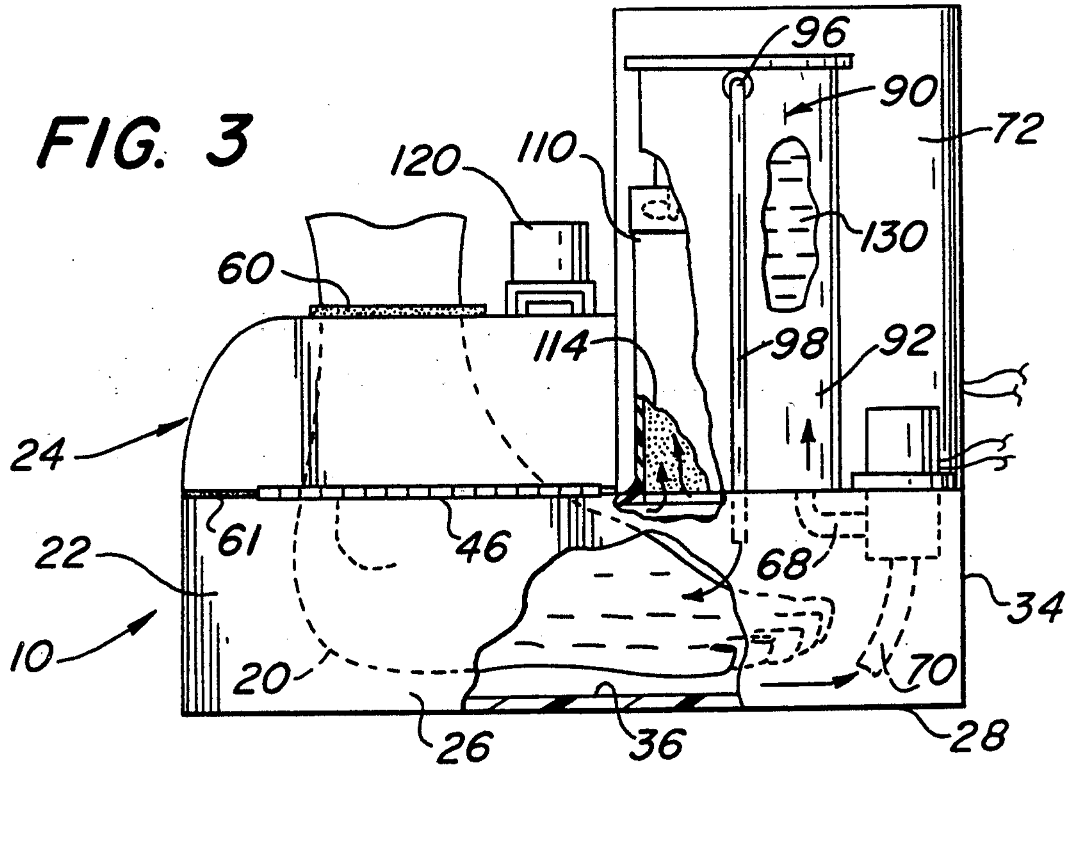
FIG. 3 is a partially broken-away end view of the device of the present invention with portions in phantom.

Referring now to various figures of the drawings where like reference numerals refer to like parts, there is shown at 10 in FIGS. 1 and 3, a device constructed in accordance with this invention for the treatment of foot 20 afflictions using a solution (not shown) containing ozone 130. The device 10 basically comprises a container 22 into which a person inserts their foot/feet 20 and which holds the liquid to be circulated (not shown) in the device 10, an ozone generator 72 to permit the transfer of ozone to the container 22, a controller 80 for regulating the production of ozone from the ozone generator 72, a pump 66 for circulating the liquid and ozone, a dispersion apparatus 90 for dispersing the ozone in the liquid, and a leakage protection component 110 to decrease the amount of ozone-containing gas from escaping from the device 10, all to be described in further detail later.

Figure 2:
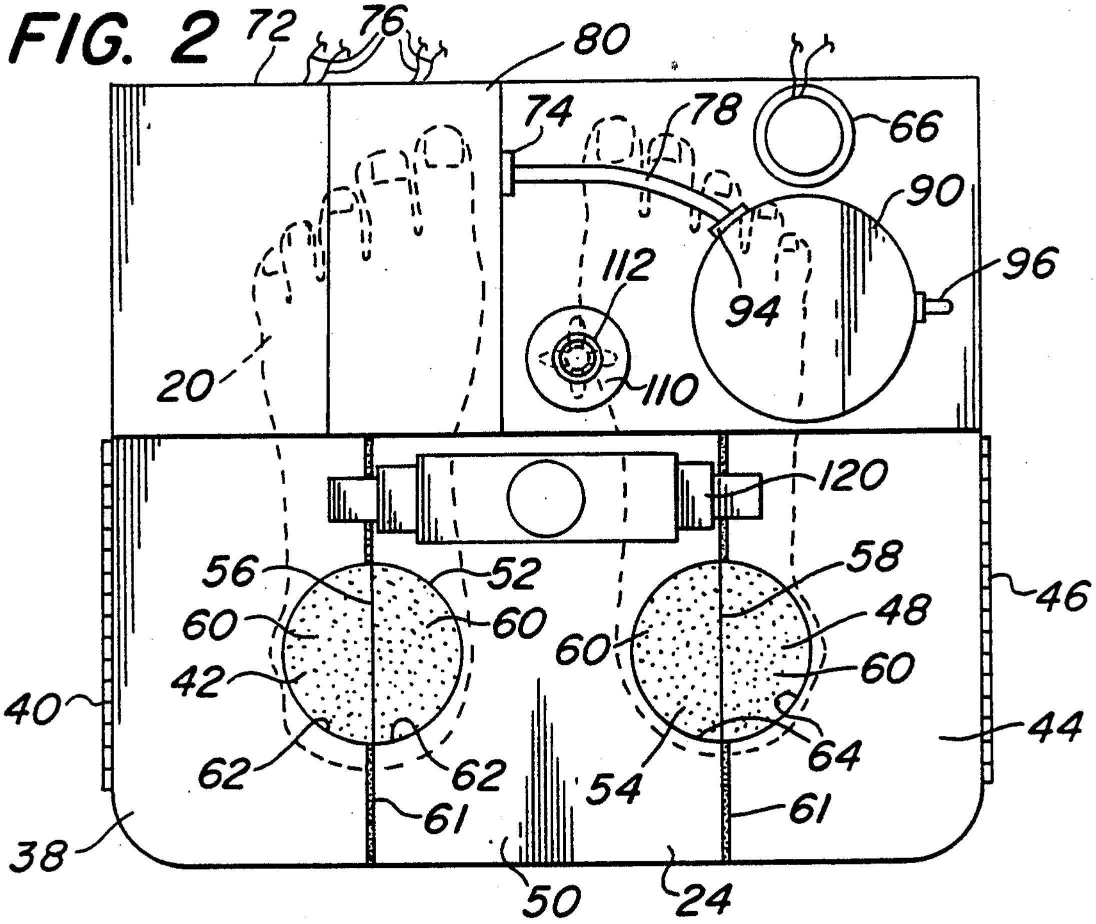
FIG. 2 is a top plan view of the device of the present invention with a person's feet drawn in phantom as inserted into the device.

As shown more clearly in FIG. the container 22 comprises an openable cover 24 and a generally rectangular base. Although any suitable cover and base arrangement may be utilized to effect the treatment of the above invention, the preferred embodiment comprises a base 26 with an edge 28 having a peripheral wall extending upwardly therefrom to form a container 22 having a left sidewall 30, a right sidewall 32 and a top 34 and bottom 36 sidewall. The openable cover 24 basically comprises a left portion 38, a right portion 44 and a central portion 50. The left portion 38 is hingedly secured to the left sidewall 30 with a left hinge 40 and has a left semi-circular opening 42 located opposite the left hinge 40. The right portion 44 is hingedly secured to the right sidewall 32 with a right hinge 46 and has a right semi-circular opening 48 located opposite the right hinge 46. As seen in FIG. 2, the central portion 50 is fixedly secured to the top sidewall 34 and abuts the left and right portions 38, 44 respectively, so that the portions of the openable cover 24 cooperate when closed, to cover the generally rectangular base 26. The central portion 50 has a first 52 and second 54 semi-circular opening. The first semicircular opening 52 is in communication with the left semicircular opening 42 of the left portion 38 to form a first generally circular opening 56 when the openable cover 24 is closed position. The second semi-circular opening 54 is in communication with the right semi-circular opening 48 of the right portion to form a second generally circular opening 58 when the openable cover 24 is closed. Each of the first and second generally circular openings have a self-sealing seal 60 secured about each of their respective inner circumferences to prevent the escape of gaseous ozone from the container and to permit a person to insert their foot/feet therethrough. Although any resilient material may be used, it is preferred that the self-sealing seal comprises flexible foam rubber. In addition, as shown in FIGS. 1 and 2, this flexible sealing material 61 is located about the internal periphery of the cover 24, where the left and right portions 38 and 44, respectively, are in close proximity to the central portion 50 in their closed orientation to prevent the escape of ozone and/or liquid during use.

As seen more clearly in FIGS. and 2, the ozone generator 72 is connected to the controller 80 and has an inlet (not shown) to admit a quantity of oxygen-containing gas (not shown) from the environment. In addition, the ozone generator 72 has an outlet 74 (FIG. 2) which communicates with the dispersion apparatus 90 to direct ozone-containing gas into the dispersion apparatus and is connected to a suitable electric source by electrical connector 76. Although any suitable ozone generator system may be used, it is preferable to use the generator produced and sold under U.S. Pat. No. 4,869,881, by Pillar Technologies Co., 475 Industrial Dr., Hartland, WI 53029. In addition, it may be desirable, depending upon the circumstances of use, to utilize gases other than ozone and/or to use liquids other than water.

As shown in FIGS. 1 and 2, the controller/indicator 80 regulates the production of ozone from the ozone generator 72 and comprises an oxidation-reduction potential indicator (not shown) in fluid communication with the liquid in the container 22 and has a display monitor 82 to monitor the electrical potential. Although any suitable indicator/controller may be utilized, it is preferable to use the oxidation-reduction potential (ORP) indicator/controller produced by the Cole-Parmer Company, 7425 N. Oak Park Avenue, Chicago, IL 60648, which has a measurement range of −1000 to +1000 mV with a 1 mV resolution. . The indicator/controller 80 will restrict the addition of the oxidation reagent (ozone) when the set upper limit is reached.

Although any range of ozone concentration may be used depending upon the circumstances of use, for the treatment of fungal infections, it is preferable that the ozone be in a concentration range of 0.1 to 0.4 mg ozone/liter water. In order to obtain this concentration range, it is necessary to set the indicator/controller 80 to a reading of 720 to 760 mV.

As seen in FIGS. 1 and 2, the dispersion apparatus 90 disperses the gaseous ozone in the liquid such as water or any other suitable liquid by permitting the ozone gas to be bubbled or mixed into the liquid in the dispersion apparatus 90. As seen in FIG. 3, the dispersion apparatus comprises a receptacle 92 to hold a quantity of liquid to be mixed with ozone 130, a first conduit 94 in fluid communication with the outlet 74 of the ozone generator 72 by tube 78 to provide a stream of ozone to the liquid in the dispersion apparatus and a second conduit 96 in fluid communication with the container 22 by tube 98 to provide a solution of ozone and liquid to the container 22. Although the ozone gas may be bubbled into the receptacle 92 in any manner, it is preferable that the ozone gas be bubbled into the receptacle 92 near its base, so that as it rises to the top of the receptacle, the rising action of the gas will facilitate its being mixed/dissolved into the liquid being used.

As shown in FIG. 3, in order to facilitate the mixing of the ozone with the liquid and bringing the ozone to the person's foot/feet 20, the device of the present invention uses a pump 66 which circulates the solution of liquid and ozone. The pump 66 has an inlet 70 in fluid communication with the container 22 and an outlet 68 in fluid communication with the receptacle 92 of the dispersion apparatus 90 and is connected to an electrical source (not shown) by electrical connector 76.

Since even small amounts of ozone can be deleterious to individuals, the device 10 further comprises a leakage protection apparatus 110 to decrease/minimize the amount of ozone-containing gas from escaping from the device 10. The leakage protection apparatus 110, as seen in FIGS. 1 and 3, comprises an activated carbon filter 114 connected to the container 22 near its uppermost portion where the gas would most likely collect, for filtering and deactivating the gaseous ozone therefrom. In addition, the leakage protection apparatus comprises a fan 112 which draws the excess ozone gas from the container 22 through the filter 114. The neutralized gaseous filtrate (ozonated) is then passed harmlessly out of the device through the vent 116 and into the surrounding atmosphere. Although any suitable material for filtering and deactivating the ozone from the device may be used, it is preferable to use a conventional activated charcoal filter.

In addition, if desirable, the device 10 may also include latch 120 (FIG. 2) which aids in keeping the left and right portions 38 and 44, of the openable cover 24 closed during generation of the ozone gas, to further minimize any potential personal exposure thereto.

The method of treating a person's foot afflictions with ozone gas in accordance with the present invention comprises the steps of placing the person's foot/feet 20 into the container 22, filling the container 22 with a liquid (not shown) to cover the afflicted portion of the person's foot/feet, generating ozone gas and mixing the ozone gas with the liquid, circulating the liquid and ozone about the person's foot/feet for a predetermined time, and then removing the person's foot/feet from the container. Although any suitable concentration of ozone may be used depending upon the circumstances of use, it is preferable that the ozone be present in a concentration in the range of 0.1 to 0.4 mg/liter of liquid, such as water. At this concentration range, it is preferable to have the person bathe their foot/feet in the ozonated liquid for approximately 5 to 10 minutes, although times may vary depending upon the degree of affliction, etc.

Without further elaboration the foregoing will so fully illustrate my invention that others may, by applying current or future knowledge, adopt the same for use under various conditions of service.

I claim:

1. A device for the treatment of foot afflictions using an aqueous solution of ozone comprising container means into which a person inserts at least one foot to be treated and for holding a liquid to be circulated in the device, the container means comprising a self-sealing means for automatically preventing the escape of ozone from the container means when the person inserts at least one of their feet therethrough, pump means for circulating the liquid and ozone in the device, ozone production means to permit the transfer of ozone to the container means, controller means for regulating the production of ozone from the ozone production means, dispersion means for dispersing the ozone in the liquid, and leakage protection means to decrease the amount of ozone-containing gas from escaping from the device.

2. The device of claim 1 wherein the container means additionally comprises an openable cover in which the self-sealing means is mounted and a container into which a person inserts at least one foot to be treated and for holding a liquid to be circulated in the device.

3. The device of claim 2 wherein the self-sealing means comprises foam rubber.

4. The device of claim 1 wherein the ozone production means comprises an ozone generator connected to the controller means and having inlet means for admitting a quantity of oxygen-containing containing gas thereto and outlet means communicating with the dispersion means for releasing ozone-containing gas into the dispersion means.

5. The device of claim 1 wherein the controller means for regulating the production of ozone from the ozone production means comprises an oxidation-reduction potential indicator in fluid communication with the container means.

6. The device of claim 1 wherein the dispersion means for dispersing the ozone in the liquid comprises a receptacle for holding a quantity of liquid to be mixed with ozone, first conduit means in fluid communication with the outlet means of the ozone generator to provide a stream of ozone to the liquid in the dispersion means, and second conduit means for providing a solution of ozone and liquid to the container means.

7. The device of claim 1 wherein the pump means for circulating the solution of liquid and ozone in the device comprises a pump having an inlet connected to the container means and an outlet connected to the receptacle of the dispersion means.

8. The device of claim 1 wherein the leakage protection means to decrease the amount of ozone-containing gas from escaping from the device comprises a filter means connected to the container means for filtering gaseous ozone therefrom.

9. The device of claim 8 wherein the filter means comprises a fan, an activated charcoal filter and a vent, wherein the fan draws gaseous ozone from the container through the activated charcoal filter and out the vent.

10. A method of treating a person's foot afflictions comprising the steps of:

a. placing at least one of the person's feet into a container;

b. filling the container with a liquid to cover the afflicted portion of the at least one of said person's feet;

c. generating ozone gas and mixing the ozone gas with the liquid to create a solution having a concentration of ozone in the range of 0.1 to 0.4 mg/liter of liquid;

d. circulating the solution about the at least one of said person's feet for a predetermined time; and e. removing the at least one of said person's feet from the container holding solution.

11. The method of claim 10 wherein the predetermined time is in the range of 5 to 10 minutes.

* * * * *